(12) United States Patent
Rogovsky (10) Patent No.: US 7,192,279 B2
(45) Date of Patent: Mar. 20, 2007

(54) DENTAL HANDPIECE

(76) Inventor: Yury Mikhailovich Rogovsky, Frunzenskaya naberezhnaya, 50-427, 119270, Moscow (RU)

( * ) Notice: Subject to any disclaimer, the term of this patent is extended or adjusted under 35 U.S.C. 154(b) by 0 days.

(21) Appl. No.: 10/653,308

(22) Filed: Sep. 2, 2003

(65) Prior Publication Data
US 2004/0214136 A1    Oct. 28, 2004

(30) Foreign Application Priority Data
Apr. 24, 2003    (RU) ............................... 2003112061

(51) Int. Cl.
*A61C 1/12*    (2006.01)
*A61C 1/05*    (2006.01)
(52) U.S. Cl. .................... 433/130; 433/29; 433/132
(58) Field of Classification Search ........ 433/131–133, 433/29, 126; 415/904
See application file for complete search history.

(56) References Cited

U.S. PATENT DOCUMENTS 3,727,312 A * 4/1973 Durante ...................... 433/130
4,281,989 A * 8/1981 Glover et al. ............... 433/130
5,052,924 A * 10/1991 Berg ............................ 433/29
5,476,380 A * 12/1995 Rosenstatter ................ 433/100
5,634,790 A * 6/1997 Pathmanabhan et al. ...... 433/29

FOREIGN PATENT DOCUMENTS

| RU | 2030903  | 3/1995 |
| RU | 2030904  | 3/1995 |
| RU | 96101748 | 5/1998 |
| RU | 95115680 | 5/1999 |

* cited by examiner

*Primary Examiner*—John J Wilson
(74) *Attorney, Agent, or Firm*—Synnestvedt & Lechner LLP; Gregory S. Bernabeo (57) ABSTRACT

A dental handpiece including a handpiece body with a head mounting seat, with a gas feeding channel, wherewith the seat is adapted to provide a full turn of the head. The head includes a turbine and an gas feeding aperture to the turbine. A micromotor is included having an inlet for feeding gas and a drive shaft for ensuring mechanical drive action. An intermediate gas feeding channel is made on the inner surface of the head mounting seat or on the outer surface of a part of the head. The drive shaft of the micromotor is connected to the head, and the inlet for feeding gas to the micrometer is connected to the gas feeding channel in the body.

25 Claims, 6 Drawing Sheets

DENTAL HANDPIECE

BACKGROUND OF THE INVENTION

1. Field of the Invention

The invention relates to medical equipment, in particular to dental handpieces.

2. Description of the Related Art

A dental handpiece is known from RU patent 2030904, issued Mar. 20, 1995. This dental handpiece comprises a handle-body with channels arranged therein for supply and discharge of air, a head with a body extending sidewise from the handle-body, the head being mounted with the possibility for turning in a sagital plane by 360° C. by means of a turning sleeve arranged in the handle-body of the handpiece and entering into engagement on one side with a screw drive mounted on the handle-body, and on the other side with a pinion connected to the body of the head, a turbine arranged in the head and mounted on bearings. The dental instrument in the known handpiece is mounted in a collet holder connected to the turbine and having therewith a common axis of rotation. The known device additionally comprises a light guide positioned inside the handle-body and the head.

A drawback of the known device is presence of the head body extending transversely to the handle-body and thus making the operation of the instrument in the patient's mouth cavity more complex. An additional drawback of the known device is absence of a possibility for structural embodiment of coinciding axis of rotation of the dental instrument and longitudinal axis of the handle-body. One more drawback of the known device is necessity to use a single light guide therein, which light guide passes through the handle inside the head what results in its twisting when the head turns, what may cause breaking of this light guide.

A dental instrument is known from a patent application RU 96101748, published May 10, 1998, this instrument comprising a head with a chuck holder for the working instrument, a collar, a body and a system for driving the chuck holder, wherein an axis of the chuck-holder of the instrument making an angle in respect to the working axis of rotation of the head, in combination with the latter and depending on the modification forms a working surface which is one from a complete circle to a complete cone with fixed working points, when the head makes a full turn about its axis.

The dental instrument known from patent application RU 96101748 has the same drawbacks as the dental handpiece known from patent RU 2030904.

Micromotors are also known from prior art and are described, for example, in generally available technical manuals and advertising materials of the Siemens, Sirona, Kawo firms. Micromotors were relatively widely used in dental equipment as a compact device providing driving action for rotating movement of a dental instrument, for example, a drill. A drawback of existing micromotors is their limited functionality when used only with mechanical dental handpieces.

SUMMARY OF THE INVENTION

Thus, the object of the present invention is to provide a dental handpiece with a swivel head which substantially does not extend outside the handpiece, thus making it possible to significantly expand possibilities of use of the dental instrument and significantly ease work therewith in a patient's mouth cavity. One more object of the present invention is to provide such a construction of the light guide, positioned inside the body, and the head of the dental handpiece, which makes possible to carry out a turn of the head in a seat of the body without subjecting the light guide to twisting or other potentially destroying actions. One more object of the instant invention is to provide a construction of a micromotor that is intended for use together with dental mechanical and also turbine handpieces that have a swivel head, virtually not extending outside the handpiece.

The term "gas," as a more general feature, is used through the description of the proposed inventions and their preferable embodiments. The proposed technical solutions are suitable for operation with any gaseous mixtures, although the gas that is used most often in dental practice is air or different water-air mixtures. Therefore, in the context of the present description, the concepts "air," "gas," and "working medium" are presumed to be equivalent.

The foregoing objects are achieved by providing a dental handpiece, comprising a head with positioned therein turbine having means for mounting a dental instrument and at least one gas feeding aperture to the turbine, a handpiece body having a head mounting seat and a gas feeding channel, wherein the head mounting seat is made adaptable for providing a full turn of the head, and at least one intermediate channel or groove for feeding gas, connecting the gas feeding channel from at least one of the apertures for feeding gas to the turbine in any position of the head when it is turned, is made on the inner surface of the head mounting seat or on the outer surface of a part of the head positioned inside the seat, thus providing the ingress of gas from the gas feeding channel into at least one gas feeding aperture to the turbine in any position of the head when it is turned.

In the proposed dental handpiece, the gas feeding aperture to the turbine may be made in the form of a nozzle, one or several outlet apertures for the discharge of the gas turning the turbine may additionally be made in the head itself, and one or several intermediate channels for the discharge of that spent gas are made in the head mounting seat and in the body of the handpiece, this ensuring the discharge of gas from at least one outlet aperture in any position of the head when it is turned.

The intermediate gas discharge channel may be made similar to the intermediate gas feeding channel on the outer surface of the part of the head that is positioned inside the seat, connecting at least one outlet aperture to the channel for the discharge of the gas in the body in any position of the head when it is turned.

Additionally the use of means in the dental handpiece for securing the head in the seat is possible, this ensuring the rapid detachment and mounting or replacement of the head, which is convenient for sterilizing the head. In order to make use of the dental handpiece easier and to reduce the danger of trauma of the cavity being treated, the outer surface of the handpiece body around the seat of the head and also the outer surface of the head may be made in such a manner that together they form the shape of a body of rotation.

The dental instrument mounting means in the dental handpiece may comprise a device ensuring fixation and release of the instrument therein from the side of the working field. Miniaturization of the head itself is achieved by this, since in the traditionally used handpieces a button on top of the head is used to release the device in which the working instrument is mounted, which results in an increase of the longitudinal and lateral dimensions of the whole construction, reducing the convenience of working in the mouth cavity and increasing the danger of trauma to the patient.

In the proposed dental handpiece the intermediate channel providing the supply of gas from the gas feeding channel to at least one nozzle may be made on the outer surface of the end face part of the head and may be straight, curved, have the shape of a ring, a flat or spatial spiral, and also any combinations of these and other known shapes.

In order to fix the head in arbitrary positions in the seat during a turn thereof, a device for discrete fixation, for example, a pin or tongue mechanism, is provided. Fixation of the head in arbitrary positions during its turn in the seat may also be provided by means of making the inner surface of the seat and the outer surface of the part of the head positioned inside the seat congruent. Such surfaces being lapped one to another provide for fixation of the head in any position when turned. In any case in order to avoid the danger of injuring the patient during use of the dental handpiece, the force of fixation is selected so that it would not be more than the force of resistance capable of stopping the turbine operating under the action of the air fed to it through a nozzle.

Rotation of the head is carried out manually or with the aid of a mechanical drive, for example a gear set, one of the gears of which is positioned on the head, the other is inside the body of the handpiece. In order to transfer the force from the drive to the head, a reducer is additionally used.

A channel for feeding a water-air mixture to the surface being treated may additionally be provided in the body of the dental handpiece, and also a light guide is mounted.

Thus, the aforesaid objects are also achieved by a dental handpiece comprising a head with a dental instrument mounted thereon, a handpiece body with a head mounting seat, the seat being adapted to provide a full turn of the head, wherein at least one first light guide having an outlet in the head mounting seat is positioned in the body of the handpiece, and at least one second light guide, having an inlet in a part of the head positioned inside the seat and an outlet on the head, is positioned in the head, wherein the outlet of at least one first light guide and the inlet of at least one second light guide are positioned at least partially opposite each other in any position of the head when it is turned.

The outlet of the first light guide and the inlet of the second light guide may be positioned on the axis of rotation of the head relative to the head mounting seat, and the head may have at least one output aperture, going through which air, turning the turbine, will blow on the outlet of the second light guide on the head, thus cleaning it of tooth dust and other impurities.

The aforesaid objects are also achieved by a dental handpiece, comprising a head with positioned therein turbine with means for mounting a dental instrument and at least one gas feeding aperture to the turbine, a handpiece body having a head mounting seat and a gas feeding channel, wherein the head mounting seat is made adaptable for providing a full turn of the head, and also comprising a micromotor having an inlet for feeding gas and an outlet, for example—a drive shaft, to provide mechanical drive action, wherein the outlet for providing mechanical drive action is connected to the head, and the inlet for feeding gas to the micromotor is connected to the gas feeding channel in the body.

The micromotor is connected to the head by means of any mechanical drive, for example gear or friction. The micromotor provides for generation of straight and reverse mechanical drive action.

Two types of micromotors are used—pneumatic in which the drive action is generated due to the gas fed to the inlet of the micromotor, or electrical, in which the drive action is produced due to electric energy fed to the micromotor. The electric micromotor is a high-revolution motor, with air, fed to a corresponding inlet, used to cool it. In accordance with this, when a pneumatic micromotor is used, the inlet for feeding gas to the micromotor is connected to the gas feeding channel in such a manner that when the micromotor for generating mechanical drive action is activated, gas is only supplied to the micromotor, while when the micromotor is turned off the gas is supplied through the gas feeding channel to the turbine. When an electric micromotor is used, when it is turned on to produce mechanical drive action, the cooling gas is supplied only to the micromotor through the inlet for feeding cooling gas, while when the micromotor is turned off—only through the gas feeding channel to the turbine.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention.

In the drawings.

DESCRIPTION OF THE PREFERRED EMBODIMENTS

Reference will now be made in detail to the present preferred embodiments of the present invention, examples of which are illustrated in the accompanying drawings.

Figure 1:
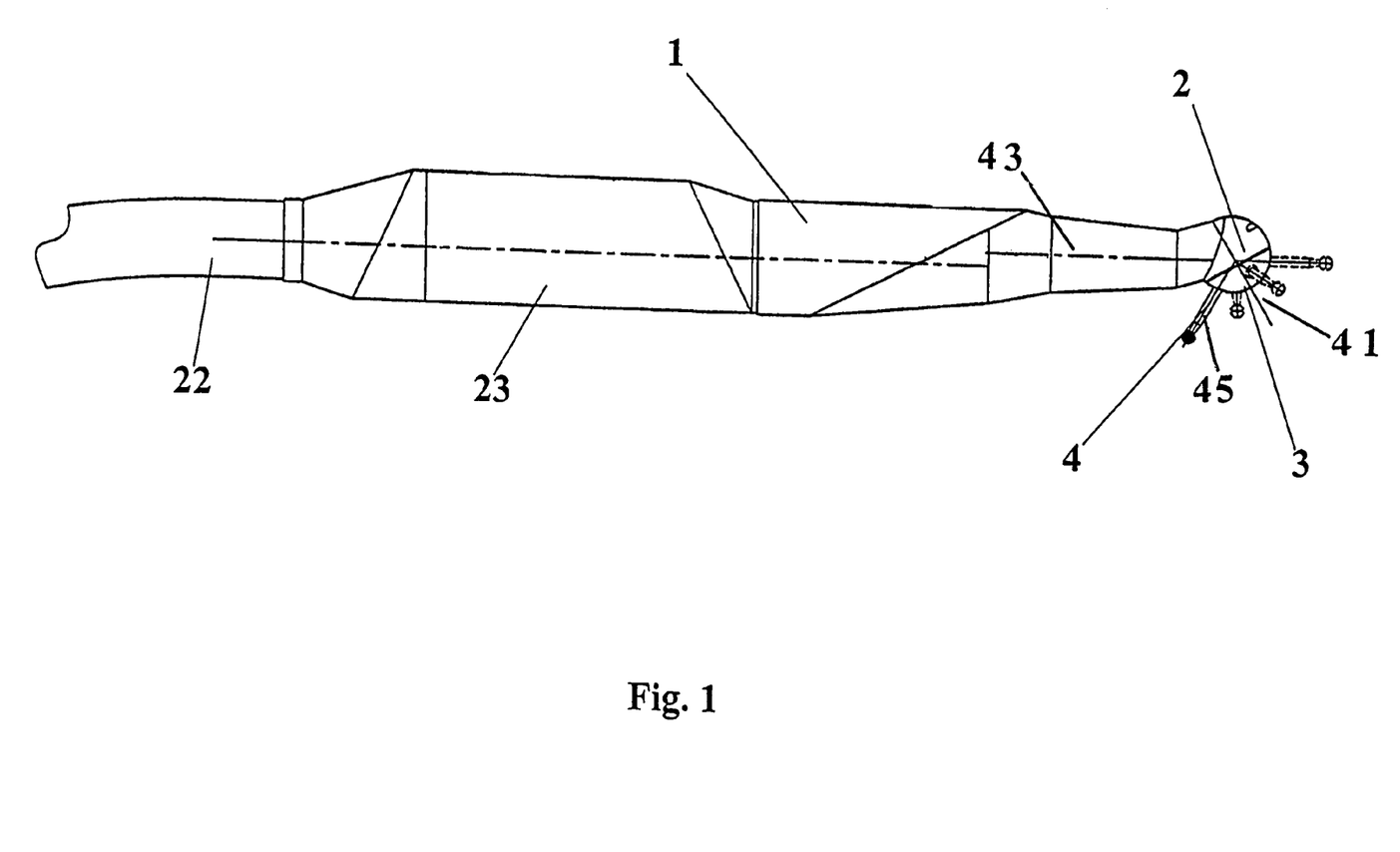
FIG. 1 shows a general view of a dental handpiece in an assembly with an arm and a body for the micromotor.

FIG. 1 presents a general view of a dental handpiece with an arm 22 and a body 23 for a micromotor 28 connected thereto. The dental handpiece has a body 1, terminating with a cup 2. There is a seat in the cup 2 of the body 1, in which seat a head 3 is turnably mounted for rotation about an axis 41. A dental instrument 4 is mounted in the head 3.

A specificity of the proposed dental handpiece is the virtually complete absence of transverse displacement of the head from the longitudinal axis 43 of the handpiece. Such a specificity makes it possible to provide a dental handpiece in which when there is a certain turn of the head 3 about axis of rotation 41, the longitudinal axis 45 of the dental instrument 4 coincides with the longitudinal axis 43 of the handpiece 1 itself.

It is desirable to made the outer surfaces of the cup 2 and the head 3 rounded, thus making working inside a mouth cavity of a patient convenient. In the embodiment shown in FIG. 1, the outer surfaces of the cup 2 and the head 3 form together in essence a spherical surface.

The dental handpiece shown in FIG. 1 is mounted on the body 23 for a micromotor, which is connected to the arm 22.

Figure 2:
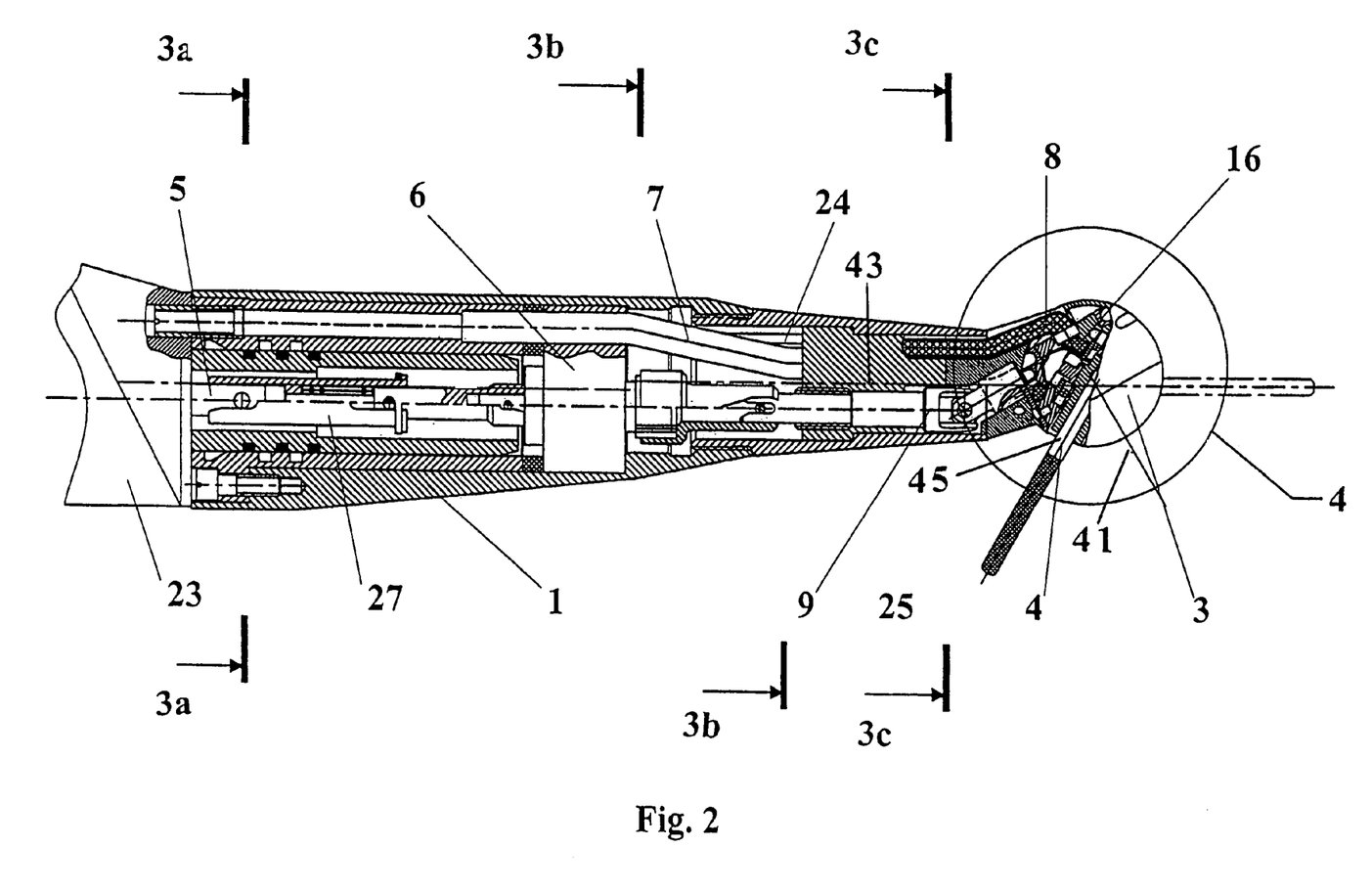
FIG. 2 shows a cross-sectional view of a dental handpiece.
Figure 3A:
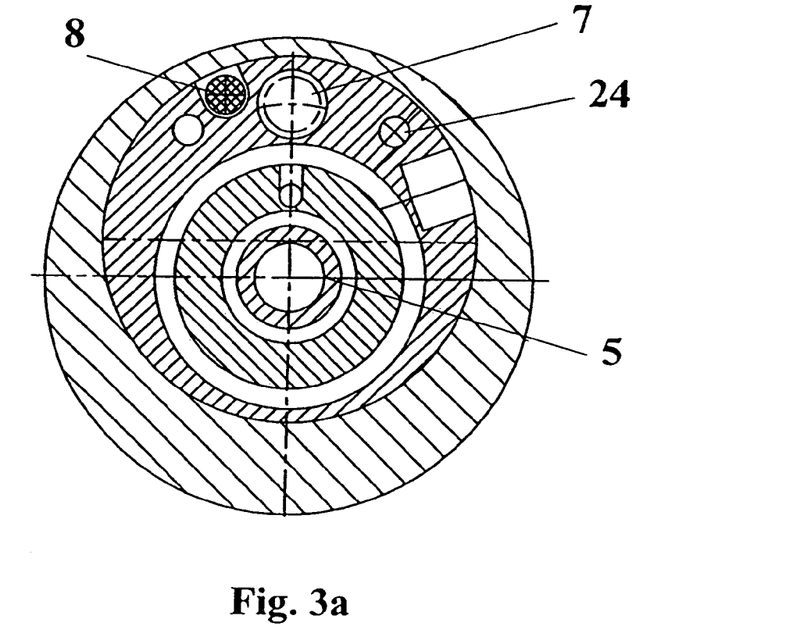
FIG. 3a, 3b, 3c show cross sections of the dental handpiece of FIG. 2.
Figure 3B:
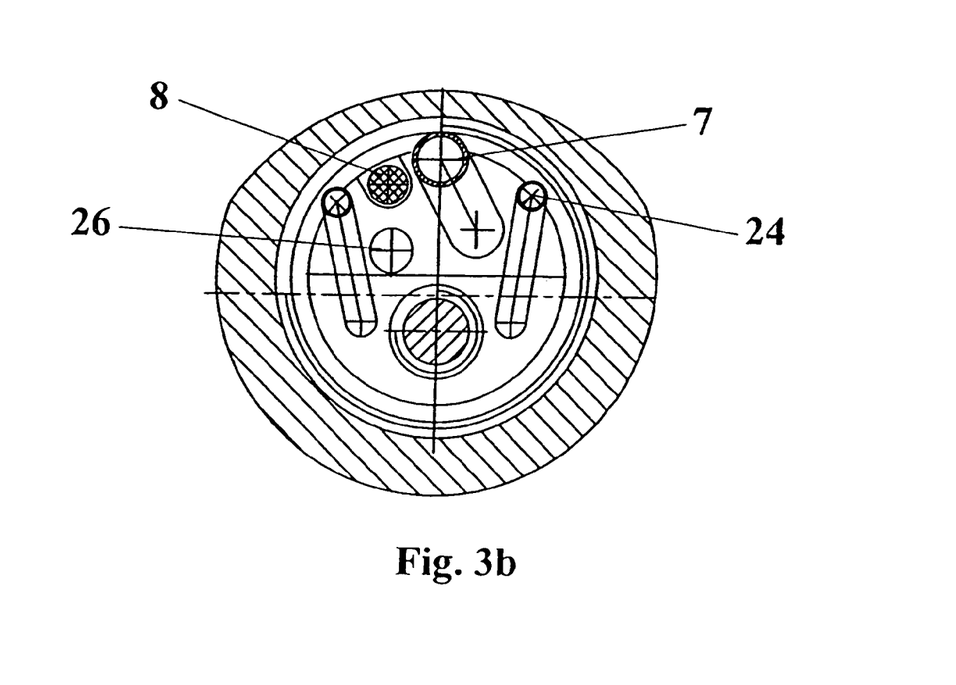
Figure 3C:
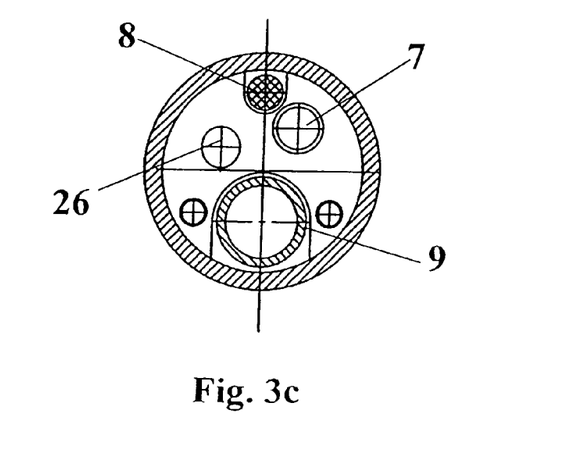

FIG. 2 shows a cross-sectional view of a dental handpiece, and the cross sections of the dental handpiece of FIG. 2, accordingly along lines A—A, B—B and C—C are shown in FIGS. 3*a*, 3*b* and 3*c*. The body 1 of the dental handpiece is mounted on the body 23 for the micromotor 28. A turbine 16 with a dental instrument 4 is mounted in the head 3. Air for accelerating the rotation of the turbine is fed along a channel 7 for feeding air, a channel 24 is additionally made in the body for feeding a water-air mixture through an aperture 25 onto the surface being treated (conditionally not shown). The drive action for turning the head is provided by a shaft 5 of the micromotor 28, which is connected to a mechanical drive 9 by means of a reducer 6.

Figure 4:
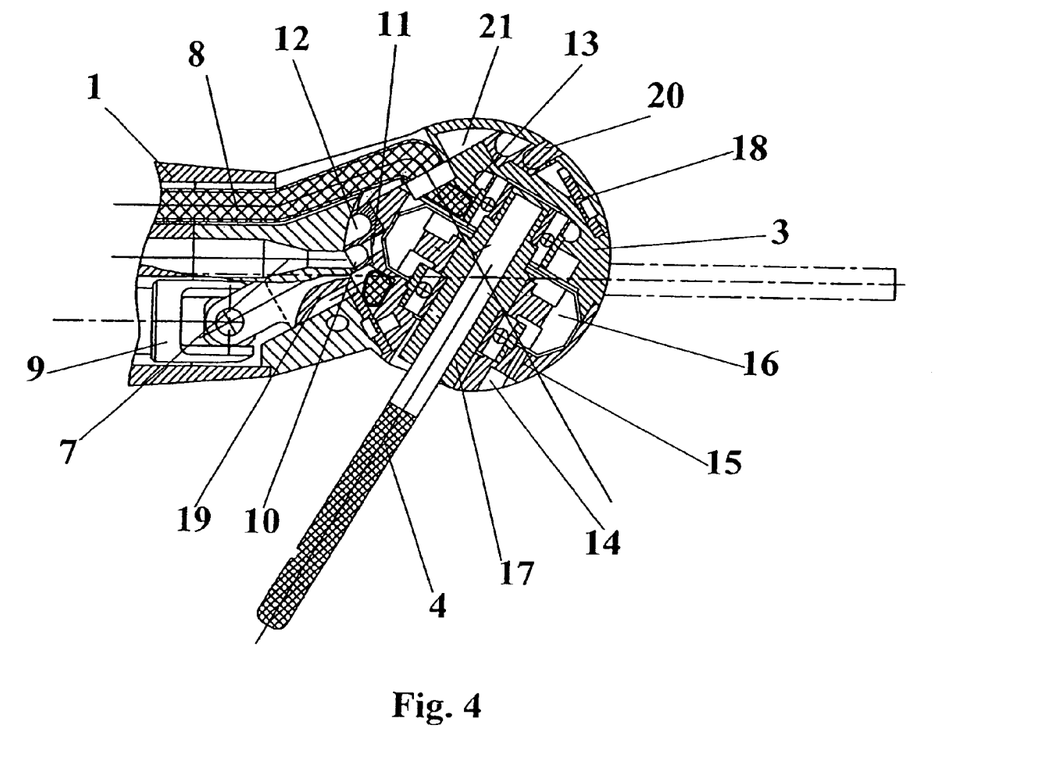
FIG. 4 shows a cross-sectional view of a part of the body of a dental handpiece with the head mounted in a seat.

A part of the body of the dental handpiece with the head mounted in a seat is more comprehensively presented in FIG. 4. The head 3 with the turbine 16 mounted therein is positioned in a seat in the body 1. A means 17 for mounting the dental instrument 4 is rigidly fixed on the turbine 16 of the head. A nozzle 11 and an intermediate channel 10, providing a supply of air from the channel 7 for feeding air through the nozzle 11 to the turbine 16, are made in the head. In the embodiment of the invention presented in FIG. 4, the intermediate channel 10 is shown annular, but other shapes of this channel are also possible, including straight, bent, in the form of a ring, flat or spatial spiral, and also in the form of any combination of these and other known shapes. The nozzle 11 may also be made of any shape. An end face 21 of the head 3 is also suitable for the intermediate channel 10 to be made thereon. In the head there is an intermediate channel 12 for discharging air from the turbine 16, which channel is connected by one or several apertures (conditionally not shown) to the cavity in which the turbine is mounted. As regards the essence of the construction, the intermediate channel 12 for discharging air is made similar to the intermediate channel 10. In the embodiment of the invention shown in FIG. 4, the intermediate channel 12 for discharging air is shown annular, but other shapes of making this channel are possible, including in the form of a flat or spatial spiral. The channel 12 for discharging air is connected to a channel 26 for discharging air that is positioned in the body. This channel 26 is more clearly presented in FIGS. 3*b* and 3*c*.

The end face part 21 of the head 3 is also suitable for having the intermediate channel 12 for discharging air made thereon. In order to prevent the head from falling out, a holder 20 is provided, which in the presented variant passes through the channel 10 and enters the body 1. Rapid detachment of the head 3, mounted in the seat, is carried out by means of moving the holder 20 to free the head 3, after which the head is easily removed from the seat. Instead of the holder 20, which is shown as a pin in the drawing, another device may be used to prevent the head from spontaneously falling out, but which does not prevent its turning in the seat, and the holder 20 itself may pass, for example, through the channel 12 or an additional aperture in the body of the head 3, and also through an aperture in the body 1 of the handpiece.

A turn of the head 3 in the seat is carried out manually or with the aid of a mechanical drive. In the case where there is no mechanical drive in the body 1, means should be provided for the discrete fixation of the head 3 in arbitrary positions when it is turned in order to provide the possibility for the dental instrument to work at any position of the head. The simplest means for providing such fixation is to make the inner surface of the head mounting seat and the outer surface of the part of the head positioned inside the seat congruent and lapped in respect to each other. In this case fixation of the head will be effected due to the force of friction between the inner surface of the seat and the outer surface of the part of the head positioned in the seat.

A spring-loaded holder 20 may also serve as the means for discrete fixation of the head.

The mechanical drive for providing a turn of the head in the embodiment presented in FIG. 4 comprises a cardan mechanism 9 and a gear pair 18 and 19. The first gear 18 of the gear pair is rigidly attached to the head 3, the second—19, is on the output shaft of the cardan mechanism 9.

The dental hand piece comprises at least two light guides positioned in the body 1 of the handpiece and in the head 3. In the embodiment presented in FIGS. 2–4, there are two light guides, wherewith the first of them—8, is positioned in the body 1, while a second light guide 13 is positioned in the head and has an outlet 14 near the dental instrument 4. The second light guide 13 is autonomous, i.e., it is not attached to the first light guide 8. In order to blow the outlet 14 of the second light guide 13, there is a channel 15 in the body of the head 3, through which air exits, cleaning the surface of the outlet 14 of impurities related to the use of the dental instrument. The first light guide 8 has an outlet in the seat, while the second light guide 13 has an inlet in the part of the head positioned inside the seat, wherewith the places for positioning the outlet of the first light guide 8 and the inlet of the second light guide 13 are selected in such a manner that with any turn of the head in the seat, there is sufficient transmission of light from one to the other respectively. In the embodiment presented in FIG. 4, the outlet of the first light guide 8 and the inlet of the second light guide 13 are shown positioned on the axis of rotation (shown in the drawing figures) of the head relative to the head mounting seat.

Access to the means 17 for mounting the dental instrument 4 is only open from the side of the working field, i.e., from the side where the dental instrument 4 is mounted. The dental instrument 4 is usually gripped in the means 17 in order to prevent its falling out of that means 17 or sliding therein. Gripping and unclamping the means 17 is carried out from the side of the working field.

Figure 5:
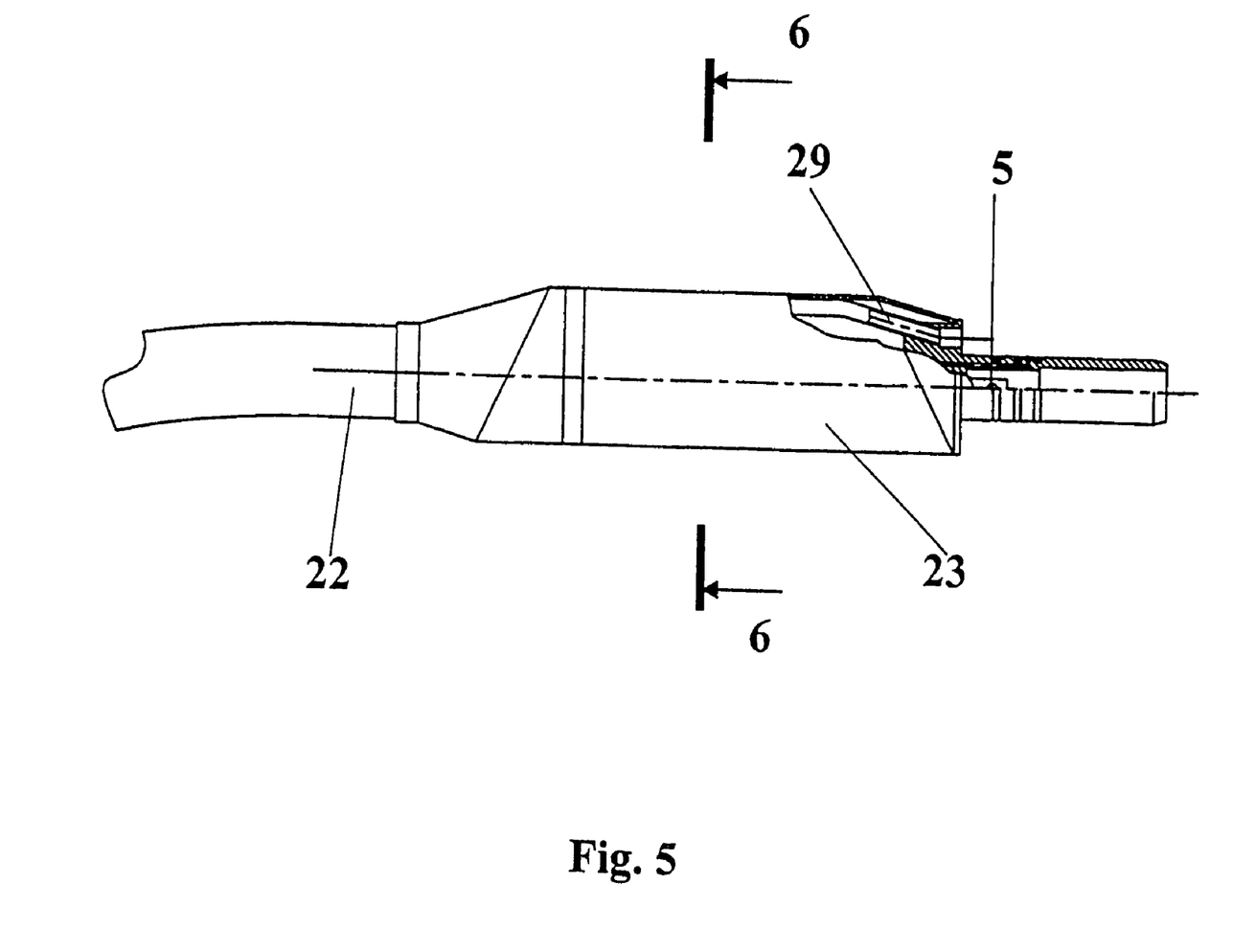
FIG. 5 shows a view with a local section of the body for the micromotor.
Figure 6:
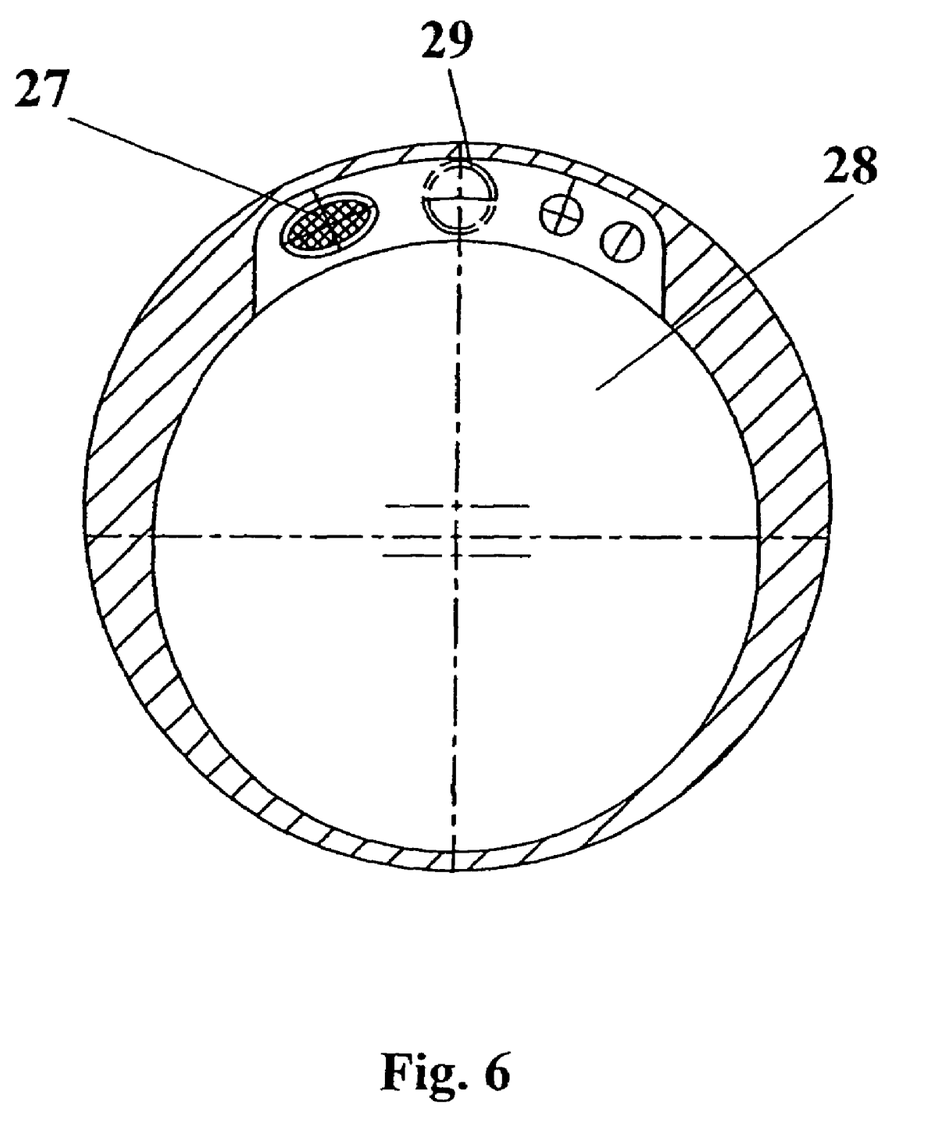
FIG. 6 shows a cross section of the body for the micromotor of FIG. 5.

The micromotor 28, which in this case is rapidly detachable, is in respect to both mechanical and turbine handpieces mounted in the body 23 as is shown in FIGS. 5 and 6. In the body 23 there is a channel 29, which when the dental handpiece is mounted on the body 23 is connected to the channel 7. There is a halogen lamp (not shown) in the body 23, the light from which enters the light guide 8. The shaft 5 of the micromotor 28 is connected by means of a bushing 27 to the reducer 6. In the case where a pneumatic micromotor is used, air, also used to activate the micromotor, is fed to the inlet of the channel 29. In the case where an electric micromotor is used, air, also used to cool the micromotor, is fed to the inlet of the channel 29.

The proposed dental handpiece works in the following manner. Air through the channels 29, 7,10 and the nozzle 11 is fed to the turbine 16, making it turn at the necessary frequency of rotation. Passing inside the cavity for the turbine 3, the spent air flow partially exits through the channels 12 and 26, and partially exits through the channel 15 and blows over the outlet 14 of the light guide 13, to which light from the halogen lamp is applied through the light guide 8. The dental instrument, oriented together with the head in a certain manner relative to the body 1, the micromotor 28 is activated. Electric power or air, depending on the type of micromotor, is fed to the micromotor 28. With any type of micromotor, its activation results in the termination of feeding air from the channel 29 and switching it to either cool the micromotor of the electric type or to generate the drive action of a pneumatic type micromotor. When the supply of air from the channel 29 ends, the turbine 16 stops.

The drive shaft 5 of the activated micromotor 28 begins to rotate, passing the rotational movement through the bushing 27 to the reducer 6 and further to the cardan 9. The gear 19 (for example—an annular gear) made on the outlet shaft of the cardan 9 and in engagement with the gear 18 (for example—an annular gear) turns the head 3 in the seat by a predetermined angle. In any new position of the head 3, the intermediate channels 10 and 12 remain connected to, respectively, channels 7 and 26, and at least a part of the outlet of the first light guide 8 remains positioned opposite at least a part of the inlet of the light guide 13.

When the micromotor 28 is turned off, the air again begins to be fed from the channel 29 through channels 7, 10 and nozzle 11 to the turbine 16, turning it to the necessary speed of rotation. The head 3 will remain in the new position due to self-braking of the mechanical drive and the turned-off micromotor.

Those skilled in the art will recognize that a variety of modifications and additions may be made to the dental handpiece without departing from the spirit of the invention. Accordingly, the invention should not be deemed limited to the particular constructions as set out in detail above and in the accompanying drawings, but instead only by a fair scope of the claims that follow along with their equivalents.

The invention claimed is:

1. A dental handpiece comprising:
   an elongated body having a longitudinal axis;
   a seat positioned at one end of said body;
   a head rotatably mounted on said seat, said head being rotatable about a first axis of rotation oriented angularly with respect to said longitudinal axis, said head having a center of rotation co-incident with said longitudinal axis;
   a dental instrument mounted on said head and rotatable about a second axis of rotation, wherein rotation of said head about said first axis of rotation changes the orientation of said second axis of rotation relatively to said longitudinal axis, said head being rotatable to an orientation wherein said second axis of rotation is coaxial with said longitudinal axis;
   an air turbine rotatably mounted within said head and connected to said dental instrument, said dental instrument being rotated by said air turbine;
   an air inlet positioned within said head in fluid communication with said turbine;
   an air outlet positioned within said head in fluid communication with said turbine;
   an inlet channel positioned within said body and said head, said channel being in fluid communication with said air inlet and providing compressed air thereto for rotating said turbine; and
   an exhaust channel positioned within said head, said exhaust channel being in fluid communication with said air outlet for discharging air from said turbine.

2. A dental handpiece according to claim 1, wherein said first axis of rotation is oriented at about a 45° angle relatively to said longitudinal axis.

3. A dental handpiece according to claim 1, wherein said head is positionable at a plurality of discrete rotational orientations.

4. A dental handpiece according to claim 1, wherein said head frictionally engages said seat, friction between said head and said seat holding said head in a predetermined rotational orientation relatively to said longitudinal axis.

5. A dental handpiece according to claim 1, wherein said second axis of rotation intersects said center of rotation of said head.

6. A dental handpiece according to claim 1, further comprising:
   a shaft rotatably mounted within said body;
   a first gear rotatably mounted within said body adjacent to said head, said first gear being engaged with said shaft such that rotation of said shaft rotates said first gear; and
   a second gear rotatably mounted within said seat and attached to said head such that rotation of second gear rotates said head about said first axis of rotation, said first gear being engaged with said second gear, wherein rotation of said shaft rotates said head about said first axis of rotation by rotating said first and second gears.

7. A dental handpiece according to claim 6, further comprising:
   a speed reducer engaged with an end of said shaft opposite said first gear; and
   a micromotor engaged with said speed reducer, wherein actuation of said micromotor rotates said shaft, rotation of said shaft rotating said head about said first axis of rotation.

8. A dental handpiece according to claim 1, wherein said head has a hemispherical outer surface.

9. A dental handpiece according to claim 8, wherein said one end of said body has a hemispherical outer surface overlying said seat.

10. A dental handpiece according to claim 9, wherein said hemispherical outer surfaces of said head and said end of said body have substantially the same radius, and wherein the centers of said outer surfaces are substantially coincident.

11. A dental handpiece according to claim 1, further comprising:
    a first light guide extending through said body and terminating adjacent to said head; and
    a second light guide positioned within said head and having a light inlet in communication with said first light guide and a light outlet positioned adjacent to said dental instrument.

12. A dental handpiece according to claim 11, further comprising a cleaning air channel positioned in said head, said cleaning air channel having a cleaning air outlet oriented so as to direct a stream of air across said light outlet.

13. A dental handpiece comprising:
    an elongated body having a longitudinal axis;
    a seat positioned at one end of said body;
    a head rotatably mounted on said seat, said head being rotatable about a first axis of rotation oriented at about a 45° angle with respect to said longitudinal axis, said head having a center of rotation co-incident with said longitudinal axis;
    a dental instrument mounted on said head and rotatable about a second axis of rotation, wherein rotation of said head about said first axis of rotation changes the orientation of said second axis of rotation relative to said longitudinal axis, said head being rotatable to an orientation wherein said second axis of rotation is coaxial with said longitudinal axis;
    an air turbine rotatably mounted within said head and connected to said dental instrument, said dental instrument being rotated by said air turbine;
    an air inlet positioned within said head in fluid communication with said turbine;
    an air outlet positioned within said head in fluid communication with said turbine;

an inlet channel positioned within said body and said head, said channel being in fluid communication with said air inlet and providing compressed air thereto for rotating said turbine; and an exhaust channel positioned within said head, said exhaust channel being in fluid communication with said air outlet for discharging air from said turbine.

14. A dental handpiece according to claim 13, wherein said head has a hemispherical outer surface.

15. A dental handpiece according to claim 14, wherein said one end of said body has a hemispherical outer surface overlying said seat.

16. A dental handpiece according to claim 15, wherein said hemispherical outer surfaces of said head and said end of said body have substantially the same radius, and wherein the centers of said outer surfaces are substantially coincident.

17. A dental handpiece comprising:

an elongated body having a longitudinal axis;

a seat positioned at one end of said body;

a head rotatably mounted on said seat, said head being rotatable about a first axis of rotation oriented at about a 45° angle with respect to said longitudinal axis, said head having a center of rotation co-incident with said longitudinal axis;

a dental instrument mounted on said head and rotatable about a second axis of rotation that intersects said center of rotation of said head, wherein rotation of said head about said first axis of rotation changes the orientation of said second axis of rotation relatively to said longitudinal axis, said head being rotatable to an orientation wherein said second axis of rotation is coaxial with said longitudinal axis;

an air turbine rotatably mounted within said head and connected to said dental instrument, said dental instrument being rotated by said air turbine;

an air inlet positioned within said head in fluid communication with said turbine;

an air outlet positioned within said head in fluid communication with said turbine;

an inlet channel positioned within said body and said head, said channel being in fluid communication with said air inlet and providing compressed air thereto for rotating said turbine; and an exhaust channel positioned within said head, said exhaust channel being in fluid communication with said air outlet for discharging air from said turbine.

18. A dental handpiece according to claim 17, wherein said head has a hemispherical outer surface.

19. A dental handpiece according to claim 18, wherein said one end of said body has a hemispherical outer surface overlying said seat.

20. A dental handpiece according to claim 19, wherein said hemispherical outer surfaces of said head and said end of said body have substantially the same radius, and wherein the centers of said outer surfaces are substantially coincident.

21. A dental handpiece comprising:

an elongated body having a longitudinal axis;

a seat positioned at one end of said body;

a head rotatably mounted on said seat, said head being rotatable about a first axis of rotation oriented angularly with respect to said longitudinal axis, said head having a center of rotation co-incident with said longitudinal axis;

a dental instrument mounted on said head and rotatable about a second axis of rotation, wherein said second axis of rotation intersects said center of rotation of said head, and rotation of said head about said first axis of rotation changes the orientation of said second axis of rotation relatively to said longitudinal axis;

an air turbine rotatably mounted within said head and connected to said dental instrument, said dental instrument being rotated by said air turbine;

an air inlet positioned within said head in fluid communication with said turbine;

an air outlet positioned within said head in fluid communication with said turbine;

an inlet channel positioned within said body and said head, said channel being in fluid communication with said air inlet and providing compressed air thereto for rotating said turbine; and an exhaust channel positioned within said head, said exhaust channel being in fluid communication with said air outlet for discharging air from said turbine.

22. A dental handpiece comprising:

an elongated body having a longitudinal axis;

a shaft rotatably mounted within said body;

a seat positioned at one end of said body;

a head rotatably mounted on said seat, said head being rotatable about a first axis of rotation oriented angularly with respect to said longitudinal axis, said head having a center of rotation co-incident with said longitudinal axis;

a first gear rotatably mounted within said body adjacent to said head, said first gear being engaged with said shaft such that rotation of said shaft rotates said first gear;

a second gear rotatably mounted within said seat and attached to said head such that rotation of second gear rotates said head about said first axis of rotation, said first gear being engaged with said second gear, wherein rotation of said shaft rotates said head about said first axis of rotation by rotating said first and second gears;

a speed reducer engaged with an end of said shaft opposite said first gear;

a micromotor engaged with said speed reducer, wherein actuation of said micromotor rotates said shaft, rotation of said shaft rotating said head about said first axis of rotation;

a dental instrument mounted on said head and rotatable about a second axis of rotation, wherein rotation of said head about said first axis of rotation changes the orientation of said second axis of rotation relatively to said longitudinal axis;

an air turbine rotatably mounted within said head and connected to said dental instrument, said dental instrument being rotated by said air turbine;

an air inlet positioned within said head in fluid communication with said turbine;

an air outlet positioned within said head in fluid communication with said turbine;

an inlet channel positioned within said body and said head, said channel being in fluid communication with said air inlet and providing compressed air thereto for rotating said turbine; and an exhaust channel positioned within said head, said exhaust channel being in fluid communication with said air outlet for discharging air from said turbine.

23. A dental handpiece comprising:

an elongated body having a longitudinal axis;

a seat positioned at one end of said body, said one end of said body having a hemispherical outer surface overlying said seat;

a head having a hemispherical outer surface and being rotatably mounted on said seat, said head being rotatable about a first axis of rotation oriented angularly with respect to said longitudinal axis, said head having a center of rotation co-incident with said longitudinal axis, said hemispherical outer surfaces of said head and said end of said body having substantially the same radius, the centers of said outer surfaces being substantially coincident;

a dental instrument mounted on said head and rotatable about a second axis of rotation, wherein rotation of said head about said first axis of rotation changes the orientation of said second axis of rotation relatively to said longitudinal axis;

an air turbine rotatably mounted within said head and connected to said dental instrument, said dental instrument being rotated by said air turbine;

an air inlet positioned within said head in fluid communication with said turbine;

an air outlet positioned within said head in fluid communication with said turbine;

an inlet channel positioned within said body and said head, said channel being in fluid communication with said air inlet and providing compressed air thereto for rotating said turbine; and an exhaust channel positioned within said head, said exhaust channel being in fluid communication with said air outlet for discharging air from said turbine.

24. A dental handpiece comprising:

an elongated body having a longitudinal axis;

a seat positioned at one end of said body, said one end of said body having a hemispherical outer surface overlying said seat;

a head having a hemispherical outer surface and being rotatably mounted on said seat, said head being rotatable about a first axis of rotation oriented at about a 45° angle with respect to said longitudinal axis, said head having a center of rotation co-incident with said longitudinal axis, said hemispherical outer surfaces of said head and said end of said body having substantially the same radius, the centers of said outer surfaces being substantially coincident;

a dental instrument mounted on said head and rotatable about a second axis of rotation, wherein rotation of said head about said first axis of rotation changes the orientation of said second axis of rotation relative to said longitudinal axis;

an air turbine rotatably mounted within said head and connected to said dental instrument, said dental instrument being rotated by said air turbine;

an air inlet positioned within said head in fluid communication with said turbine;

an air outlet positioned within said head in fluid communication with said turbine;

an inlet channel positioned within said body and said head, said channel being in fluid communication with said air inlet and providing compressed air thereto for rotating said turbine; and an exhaust channel positioned within said head, said exhaust channel being in fluid communication with said air outlet for discharging air from said turbine.

25. A dental handpiece comprising:

an elongated body having a longitudinal axis;

a seat positioned at one end of said body, said one end of said body having a hemispherical outer surface overlying said seat;

a head having a hemispherical outer surface and being rotatably mounted on said seat, said head being rotatable about a first axis of rotation oriented at about a 45° angle with respect to said longitudinal axis, said head having a center of rotation co-incident with said longitudinal axis, said hemispherical outer surfaces of said head and said end of said body having substantially the same radius, the centers of said outer surfaces being substantially coincident;

a dental instrument mounted on said head and rotatable about a second axis of rotation that intersects said center of rotation of said head, wherein rotation of said head about said first axis of rotation changes the orientation of said second axis of rotation relatively to said longitudinal axis;

an air turbine rotatably mounted within said head and connected to said dental instrument, said dental instrument being rotated by said air turbine;

an air inlet positioned within said head in fluid communication with said turbine;

an air outlet positioned within said head in fluid communication with said turbine;

an inlet channel positioned within said body and said head, said channel being in fluid communication with said air inlet and providing compressed air thereto for rotating said turbine; and an exhaust channel positioned within said head, said exhaust channel being in fluid communication with said air outlet for discharging air from said turbine.

\* \* \* \* \*